(12) United States Patent
Swerdlow

(10) Patent No.: US 10,793,904 B2
(45) Date of Patent: Oct. 6, 2020

(54) METHODS FOR SEQUENCING A POLYNUCLEOTIDE TEMPLATE

(71) Applicant: Illumina Cambridge Limited, Saffron Walden (GB)

(72) Inventor: Harold Philip Swerdlow, Saffron Walden (GB)

(73) Assignee: Illumina Cambridge Limited, Cambridge (GB)

(*) Notice: Subject to any disclaimer, the term of this patent is extended or adjusted under 35 U.S.C. 154(b) by 231 days.

(21) Appl. No.: 15/677,788

(22) Filed: Aug. 15, 2017

(65) Prior Publication Data

US 2017/0342482 A1 Nov. 30, 2017

Related U.S. Application Data

(63) Continuation of application No. 11/989,170, filed as application No. PCT/GB2006/002709 on Jul. 20, 2006, now Pat. No. 9,765,391.

(30) Foreign Application Priority Data

Jul. 20, 2005 (GB) .................................. 0514935.6

(51) Int. Cl.
  *C12P 19/34* (2006.01)
  *C12Q 1/6869* (2018.01)
  *C12Q 1/6853* (2018.01)

(52) U.S. Cl.
  CPC ......... *C12Q 1/6869* (2013.01); *C12Q 1/6853* (2013.01)

(58) Field of Classification Search
  USPC .......... 435/6.1, 6.11, 6.12, 91.1, 91.2, 91.51, 435/183; 436/94, 501; 536/23.1, 24.3, 536/24.33, 25.3
  See application file for complete search history.

(56) References Cited

U.S. PATENT DOCUMENTS

| | | |
|---|---|---|
| 5,075,216 A | 12/1991 | Innis et al. |
| 5,118,604 A | 6/1992 | Weissman et al. |
| 5,302,509 A | 4/1994 | Cheeseman |
| 5,308,751 A | 5/1994 | Ohkawa et al. |
| 5,547,839 A | 8/1996 | Dower et al. |
| 5,616,478 A | 4/1997 | Chetverin et al. |
| 5,629,158 A | 5/1997 | Uhlen |
| 5,641,658 A | 6/1997 | Adams et al. |
| 5,800,992 A | 9/1998 | Fodor et al. |
| 5,837,466 A | 11/1998 | Lane et al. |
| 5,922,574 A | 7/1999 | Minter |
| 5,935,788 A | 8/1999 | Burmer et al. |

(Continued)

FOREIGN PATENT DOCUMENTS

| | | |
|---|---|---|
| DE | 3839397 A1 | 5/1990 |
| DE | 10051564 A1 | 8/2002 |

(Continued)

OTHER PUBLICATIONS

EP Patent Application No. 10 00 0700.4, filed Jul. 20, 2006; Notice of Opposition dated May 23, 2016; 7 pages.

(Continued)

*Primary Examiner* — Frank W Lu
(74) *Attorney, Agent, or Firm* — Mueting Raasch Group

(57) ABSTRACT

The invention relates to methods for pairwise sequencing of a polynucleotide template which result in the sequential determination of nucleotide sequence in two distinct and separate regions of the polynucleotide template.

18 Claims, 6 Drawing Sheets

(56) References Cited

U.S. PATENT DOCUMENTS

| | | | |
|---|---|---|---|
| 5,976,802 A | 11/1999 | Ansorge et al. |
| 5,981,186 A | 11/1999 | Gabe et al. |
| 6,060,288 A | 5/2000 | Adams et al. |
| 6,090,592 A | 7/2000 | Adams et al. |
| 6,107,023 A | 8/2000 | Reyes et al. |
| 6,251,610 B1 | 6/2001 | Gupte et al. |
| 6,265,193 B1 | 7/2001 | Brandis et al. |
| 6,322,971 B1 | 11/2001 | Chetverin et al. |
| 6,326,489 B1 | 12/2001 | Church et al. |
| 6,361,947 B1 | 3/2002 | Dong et al. |
| 6,511,803 B1 | 1/2003 | Church et al. |
| 6,548,021 B1 | 4/2003 | Church et al. |
| 6,613,513 B1 | 9/2003 | Parce |
| 7,115,400 B1 | 10/2006 | Adessi et al. |
| 7,767,400 B2 | 8/2010 | Harris |
| 9,765,391 B2 | 9/2017 | Swedlow |
| 2001/0036629 A1 | 11/2001 | Dower et al. |
| 2002/0055100 A1 | 5/2002 | Kawashima et al. |
| 2002/0061532 A1 | 5/2002 | Adams et al. |
| 2002/0098499 A1 | 7/2002 | Asp et al. |
| 2002/0164591 A1 | 11/2002 | Brandis et al. |
| 2003/0013089 A1 | 1/2003 | Fisher et al. |
| 2003/0022207 A1 | 1/2003 | Balasubramanian et al. |
| 2003/0044781 A1 | 3/2003 | Korlach et al. |
| 2003/0064366 A1 | 4/2003 | Hardin et al. |
| 2003/0082576 A1 | 5/2003 | Jones et al. |
| 2003/0108867 A1 | 6/2003 | Chee et al. |
| 2003/0138809 A1 | 7/2003 | Williams et al. |
| 2003/0186256 A1 | 10/2003 | Fischer |
| 2004/0002090 A1 | 1/2004 | Mayer et al. |
| 2004/0038289 A1 | 2/2004 | O'Donnell et al. |
| 2004/0096853 A1 | 5/2004 | Mayer |
| 2004/0126765 A1 | 7/2004 | Adams |
| 2004/0197802 A1 | 10/2004 | Dahl et al. |
| 2005/0100900 A1 | 5/2005 | Kawashima et al. |
| 2005/0148002 A1 | 7/2005 | Dower et al. |
| 2005/0186576 A1 | 8/2005 | Chan et al. |
| 2006/0024681 A1 | 2/2006 | Smith et al. |
| 2006/0035233 A1 | 2/2006 | Gormley et al. |
| 2006/0134633 A1 | 6/2006 | Chen et al. |
| 2006/0147935 A1 | 7/2006 | Linnarsson |
| 2006/0292611 A1 | 12/2006 | Berka et al. |
| 2007/0128624 A1 | 6/2007 | Gormley et al. |
| 2008/0009420 A1 | 1/2008 | Schroth et al. |
| 2008/0131939 A1 | 6/2008 | Roper |

FOREIGN PATENT DOCUMENTS

| | | |
|---|---|---|
| EP | 0224126 A2 | 6/1987 |
| EP | 0356021 A2 | 2/1990 |
| EP | 0374665 A2 | 6/1990 |
| EP | 0438292 A2 | 7/1991 |
| EP | 0534858 A1 | 3/1993 |
| EP | 0665293 A2 | 8/1995 |
| EP | 0763135 A1 | 3/1997 |
| EP | 1256632 A2 | 11/2002 |
| EP | 0201184 B2 | 8/2004 |
| EP | 1591541 A2 | 11/2005 |
| EP | 1647602 A1 | 4/2006 |
| EP | 2032686 A2 | 3/2009 |
| GB | 0205153.0 A | 4/2002 |
| GB | 2398383 A | 8/2004 |
| GB | 2412170 A | 9/2005 |
| GB | 0522310.2 A | 12/2005 |
| WO | WO 89/01050 A1 | 2/1989 |
| WO | WO 89/09282 A2 | 10/1989 |
| WO | WO 90/04652 A1 | 5/1990 |
| WO | WO 92/02635 A1 | 2/1992 |
| WO | WO 92/10587 A1 | 6/1992 |
| WO | WO 93/04199 A2 | 3/1993 |
| WO | WO 94/02634 A1 | 2/1994 |
| WO | WO 95/33073 A1 | 12/1995 |
| WO | WO 96/04404 A1 | 2/1996 |
| WO | WO 96/32504 A2 | 10/1996 |
| WO | WO 98/36094 A1 | 8/1998 |
| WO | WO 98/44151 A1 | 10/1998 |
| WO | WO 98/44152 A1 | 10/1998 |
| WO | WO 00/06770 A1 | 2/2000 |
| WO | WO 00/18957 A1 | 4/2000 |
| WO | WO 00/75374 A1 | 12/2000 |
| WO | WO 01/48184 A2 | 7/2001 |
| WO | WO 01/49882 A1 | 7/2001 |
| WO | WO 01/57248 A2 | 8/2001 |
| WO | WO 01/79553 A2 | 10/2001 |
| WO | WO 02/046456 A1 | 6/2002 |
| WO | WO 02/061127 A2 | 8/2002 |
| WO | WO 03/056030 A2 | 7/2003 |
| WO | WO 03/074734 A2 | 9/2003 |
| WO | WO 2004/018497 A2 | 3/2004 |
| WO | WO 2004/070005 A2 | 8/2004 |
| WO | WO 2004/072294 A2 | 8/2004 |
| WO | WO 2004/076683 A2 | 9/2004 |
| WO | WO 2005/003375 A2 | 1/2005 |
| WO | WO 2005/021786 A1 | 3/2005 |
| WO | WO 2005/040425 A2 | 5/2005 |
| WO | WO 2005/042781 A2 | 5/2005 |
| WO | WO 2005/047301 A1 | 5/2005 |
| WO | WO 2005/068656 A1 | 7/2005 |
| WO | WO 2005/093094 A2 | 10/2005 |
| WO | WO 2006/110855 A2 | 10/2006 |
| WO | WO 2006/135342 A1 | 12/2006 |
| WO | WO 2007/010251 A2 | 1/2007 |
| WO | WO 2007/010252 A1 | 1/2007 |
| WO | WO 2007/010263 A2 | 1/2007 |
| WO | WO 2007/052006 A2 | 5/2007 |
| WO | WO 2007/076726 A1 | 7/2007 |
| WO | WO 2007/091077 A1 | 8/2007 |
| WO | WO 2007/107710 A1 | 9/2007 |
| WO | WO 2007/111937 A1 | 10/2007 |
| WO | WO 2008/002502 A2 | 1/2008 |
| WO | WO 2009/097626 A2 | 8/2009 |

OTHER PUBLICATIONS

Adessi et al., "Solid phase DNA amplification: characterization of primer attachment and amplification mechanisms," *Nucleic Acids Research*, 28(e87):1-8 (2000).

Bennett et al., "Toward the $1000 human genome," *Pharmacogenomics*, 6:373-382 (2005).

Braslavsky et al., "Sequence information can be obtained from single DNA molecules," *Proc. Natl. Acad. Sci.*, 100:3960-3964 (2003).

Brenner et al., "Gene expression analysis by massively parallel signature sequencing (MPSS) on microbead arrays" Jun. 2000; *Nat Biotechnol*, 18(6):630-4.

Cheng et al., "Chip PCR. II. Investigation of different PCR amplification systems in microfabricated silicon-glass chips," *Nucleic Acids Research*, 24:380-385 (1996).

"Chromosome 12 (human)," Wikipedia.com; accessed Apr. 18, 2015.

Dubiley et al., "Polymorphism analysis and gene detection by minisequencing on an array of gel-immobilized primers," *Nucleic Acids Research*, 27(e19):i-vi (1999).

Fu et al., "Sequencing double-stranded DNA by strand displacement," *Nucleic Acids Research*, 25:677-679 (1997).

Helfman et al., "Identification of clones that encode chicken tropomyosin by direct immunological screening of a cDNA expression library," *Proc. Natl. Acad. Sci.*, 80:31-35 (1983).

International Human Genome Sequencing Consortium, "Finishing the euchromatic sequence of the human genome", Oct. 21, 2004, *Nature*, 431:931-45.

Kalisch et al., "Covalently linked sequencing primer linkers (splinkers) for sequence analysis of restriction fragments," *Gene*, 44:263-270 (1986).

Kaur et al., "Novel amplification of DNA in a hairpin structure: towards a radical elimination of PCR errors from amplified DNA" 2003 *Nucleic Acids Research* 31(6):e26.

Kent et al., "Assembly of the Working Draft of the Human Genome with GigAssembler", 2001, *Genome Res.*, 11:1541-8.

(56) References Cited

OTHER PUBLICATIONS

Kimmel et al., "Preparation of cDNA and the Generation of cDNA Libraries: Overview," *Methods in Enzymology*, 152:307-316 (1987).
Kinzler et al., "Whole genome PCR: application to the identification of sequences bound by gene regulatory protiens," *Nucleic Acids Research*, 17:3645-3653 (1989).
Lucito et al., "Genetic analysis using genomic representations," *Proc. Natl. Acad. Sci.*, 95:4487-4492 (1998).
Margulies et al., "Genome Sequencing in microfabricated high-density picolitre reactors," *Nature*, 437:376-380 (2005).
Matsunaga et al., "Selecting and amplifying one fragment from a DNA fragment mixture by polymerase chain reaction with a pair of selective primers," *Electrophoresis*, 17:1833-1840 (1996).
Maxam et al., "A new method for sequencing DNA," *Proceedings of the National Academy of Sciences*, Feb. 1977; 74(2):560-564.
Mir et al., "Sequencing by cyclic ligation and cleavage (CycLiC) directly on microarray template," *Nucleic Acids Research*, Nov. 2008; 37(1):e5-1.
Mitra et al., "Fluorescent in situ sequencing on polymerase colonies" Sep. 1, 2003 *Analytical Biochemistry* 320(1):55-65.
Mullikin et al., "The Phusion Assembler", 2003, *Genome Res.*, 13:81-90.
Ng et al., "Multiplex sequencing of paired-end ditags (MS-PET): a strategy for the ultra-high-throughput analysis of transcriptomes and genomes," *Nucleic Acids Research*, 34(e84):1-10 (2006).
Oroskar et al., "Detection of immobilized amplicons of ELISA-like techniques," *Clinical Chemistry*, 42:1547-1555 (1996).
Roach et al., "Pairwise End Sequencing: A Unified Approach to Genomic Mapping and Sequencing," *Genomics*, 26:345-353 (1995).
Ruparel et al., "Design and synthesis of a 3'-O-allyl photocleavable fluorescent nucleotide as a reversible terminator for DNA sequencing by synthesis" Apr. 26, 2005 *Proc Natl Acad Sci U S A* 102(17):5932-7. Epub Apr. 13, 2005.

Saiki et al., "Analysis of enzymatically amplified beta-globin and HLA-DQ DNA with allele-specific oligonucleotide probes," *Nature*, 324:163-166 (1986).
Saiki et al., "Primer-Directed Enzymatic Amplification of DNA with a Thermostable DNA," *Science*, 239:487-491 (1988).
San Luis et al., "Analysis of a gene (vch) encoding hemolysin isolated and sequenced from Vibrio campbellii," *J. Gen. Appl. Microbiol.*, 52:303-313 (2006).
Sanger et al., "Cloning in Single-stranded Bacteriophage as an Aid to Rapid DNA Sequencing," *J. Mol. Biol.*, 143:161-178 (1980).
Shapero et al., "SNP Genotyping by Multiplexed Solid-Phase Amplification and Fluorescent Minisequencing," *Genome Research*, 11:1926-1934 (2001).
Shendure et al., "Accurate Multiplex Polony Sequencing of an Evolved Bacterial Genome," *Science*, 309:1728-1732 (2005).
Shi, "Enabling Large-Scale Pharmacogenetic Studies by High-Throughput Mutation Detection and Genotyping Technologies," *Clinical Chemistry*, 47:164-172 (2001).
Siegel et al., "Modeling the Feasibility of Whole Genome Shotgun Sequencing Using a Pairwise End Strategy", 2000, *Genomics*, 68:237-46.
Solexa, Solexa Application Note: DNA Sequencing (2006).
Sterky et al., "Direct sequencing of bacterial artificial chromosomes (BACs) and prokaryotic genomes by biotin-capture PCR," *Journal of Biotechnology*, 60:119-129 (1998).
Strick et al., "Stress-Induced Structural Transitions in DNA and Proteins," *Annu. Rev. Biophys. Biomol. Struct.*, 29:523-543 (2000).
Velculescu et al., "Serial Analysis of Gene Expression," *Science*, 270:484-487 (1995).
Waterston et al., "On the sequencing of the human genome" Mar. 19, 2002 *Proc Natl Acad Sci U S A* 99(6):3712-6. Epub Mar. 5, 2002.
Westin et al., "Anchored multiplex amplification on a microelectronic chip array," *Nature Biotechnology*, 18:199-204 (2000).
Wiemann et al., "Doublex Fluorescent DNA Sequencing: Two Independent Sequences Obtained Simultaneously in One Reaction with Internal Labeling and Unlabeled Primers," *Analytical Biochemistry*, 234:166-174 (1996).

METHODS FOR SEQUENCING A POLYNUCLEOTIDE TEMPLATE

CROSS-REFERENCE TO RELATED APPLICATIONS

This is a continuation application of U.S. patent application Ser. No. 11/989,170, filed Aug. 10, 2010, now U.S. Pat. No. 9,765,391, which is the § 371 U.S. National Stage Application of International Application No. PCT/GB2006/002709, filed Jul. 20, 2006, which claims the benefit of Great Britain Application Serial No. 0514935.6, filed Jul. 20, 2005, each of which is incorporated herein by reference in its entirety.

FIELD OF THE INVENTION

The invention relates to methods for pairwise sequencing of a polynucleotide template, which methods result in the sequential determination of nucleotide sequence in two distinct and separate regions of the polynucleotide template.

BACKGROUND TO THE INVENTION

Advances in the study of biological molecules have been led, in part, by improvement in technologies used to characterise the molecules or their biological reactions. In particular, the study of the nucleic acids DNA and RNA has benefited from developing technologies used for sequence analysis.

U.S. Pat. No. 5,302,509 describes a method for sequencing a polynucleotide template which involves performing multiple extension reactions using a DNA polymerase or DNA ligase to successively incorporate labelled polynucleotides complementary to a template strand. In such a "sequencing by synthesis" reaction a new polynucleotide strand based-paired to the template strand is built up in the 5' to 3' direction by successive incorporation of individual nucleotides complementary to the template strand. The substrate nucleoside triphosphates used in the sequencing reaction are labelled at the 3' position with different 3' labels, permitting determination of the identity of the incorporated nucleotide as successive nucleotides are added.

In order to carry out accurate sequencing a reversible chain-terminating structural modification or "blocking group" may be added to the substrate nucleosides to ensure that nucleotides are incorporated one at a time in a controlled manner. As each single nucleotide is incorporated, the blocking group prevents any further nucleotide incorporation into the polynucleotide chain. Once the identity of the last-incorporated labelled nucleotide has been determined the label moiety and blocking group are removed, allowing the next blocked, labelled nucleotide to be incorporated in a subsequent round of sequencing.

In certain circumstances the amount of sequence data that can be reliably obtained with the use of sequencing-by-synthesis techniques, particularly when using blocked, labelled nucleotides, may be limited, typically to around 25-30 cycles of incorporation. Whilst sequencing "runs" of this length are extremely useful, particularly in applications such as, for example, SNP analysis and genotyping, it would be advantageous in many circumstances to be able to reliably obtain further sequence data for the same template molecule.

The technique of "paired-end" or "pairwise" sequencing is generally known in the art of molecular biology, particularly in the context of whole-genomic shotgun sequencing (Siegel A. F. et al., Genomics. 2000, 68: 237-246; Roach J. C. et al., Genomics. 1995, 26: 345-353). Paired-end sequencing allows the determination of two "reads" of sequence from two places on a single polynucleotide template. The advantage of the paired-end approach is that there is significantly more information to be gained from sequencing two stretches each of "n" bases from a single template than from sequencing "n" bases from each of two independent templates in a random fashion. With the use of appropriate software tools for the assembly of sequence information (Millikin S. C. et al., Genome Res. 2003, 13: 81-90; Kent, W. J. et al., Genome Res. 2001, 11: 1541-8) it is possible to make use of the knowledge that the "paired-end" sequences are not completely random, but are known to occur on a single template, and are therefore very close in the genome. This information has been shown to greatly aid the assembly of whole genome sequence into a consensus sequence.

Paired-end sequencing has typically been performed by making use of specialized circular shotgun cloning vectors known in the art. After cutting the vector at a specific single site, the template DNA to be sequenced (typically genomic DNA) is inserted into the vector and the ends resealed to form a new construct. The vector sequences flanking the insert DNA include binding sites for sequencing primers which permit sequencing of the insert DNA on opposite strands.

A disadvantage of this approach is that it requires time-consuming cloning of the DNA templates it is desired to sequence into an appropriate sequencing vector. Furthermore, because of the need to clone the DNA template into a vector in order to position binding sites for sequencing primers at both ends of the template fragment it is extremely difficult to make use of array-based sequencing techniques. With array-based techniques it is generally only possible to sequence from one end of a nucleotide template, this often being the end proximal to the point of attachment to the array.

With the use of hairpin nucleic acid anchors or double stranded nucleic acid anchors (such as those described in the applicant's co-pending International application published as WO 01/57248), one end of a template immobilised on an array may be "covalently closed" giving a free 3' end which permits sequencing of the 5' overhanging template strand by successive incorporation of nucleotides. However, given that the distal portions (distal from the point of attachment to the array) of such immobilised templates are generally single-stranded and that the sequence of the template is usually unknown prior to immobilisation on the array, it is not straightforward to devise means for determining the sequence of the distal end of the immobilised template, beyond the first "run" of sequence that can be obtained from the free 3' end provided by the anchor. It is not possible simply to design a sequencing primer complementary to a region of the template whose sequence is unknown.

WO 2004/070005 describes a method for double-ended sequencing of a polynucleotide template which can be carried out on a solid support. The method relies on simultaneous hybridisation of two or more primers to a target polynucleotide in a single primer hybridization step. Following the hybridization step, all of the primers hybridized to the template are blocked except for one, which has a free 3' hydroxyl group which serves as an initiation point for a first sequencing reaction. Sequencing proceeds until no further chain elongation is possible, or else the sequencing reaction is terminated. Then one of the blocked primers is unblocked to give a free 3' hydroxyl and a second sequencing reaction is performed from this initiation point. An advantage of this approach is that there is no need to perform any denaturation and re-hybridization steps between the first and second sequencing reactions, as the two primers providing the initiation points are annealed in a single hybridisation step. Thus, the template remains intact and attached to the solid support throughout.

A major drawback of this approach based in hybridisation of blocked and unblocked primers is that it is necessary to know the sequence of at least two regions of the polynucleotide template to be sequenced in order to design two or more suitable primers capable of binding to the target. If the method is to be used to sequence polynucleotides of unknown sequence then it is necessary to carry out sample preparation steps in order to add regions of known sequence to the polynucleotide to be sequenced in order to provide the necessary primer-binding sites. This can be achieved, for example, by amplification or by sub-cloning a template of unknown sequence into a vector in order to add known sequences onto the 5' and 3' ends of the template.

The present inventors have sought to develop techniques which generally permit the paired-end or pairwise sequencing approach to be used without any knowledge of the sequence at the distal end of the template and without the need for any intermediate cloning of the template into a vector. Such techniques would permit pairwise sequencing to be used in conjunction with a wide range of array-based sequencing technologies, including single molecule arrays as well as clustered arrays.

DESCRIPTION OF THE INVENTION

In accordance with a first aspect of the invention there is provided a method for pairwise sequencing of a polynucleotide template, the method comprising:

(a) providing a polynucleotide template having a first free 3' hydroxyl group which is positioned to initiate sequencing of a first region for sequence determination on a first template strand, (b) carrying out a first sequencing reaction by sequential addition of nucleotides to the first free 3' hydroxyl group to determine the sequence of the first template strand in the first region, (c) generating a second free 3' hydroxyl group within the polynucleotide template at a nucleotide position which is spaced apart from the last nucleotide added in the sequencing reaction of step (b), wherein the second free 3' hydroxyl group is positioned to initiate sequencing of a second region for sequence determination on a second template strand, and wherein the second free hydroxyl group is in continuous covalent linkage with the last nucleotide added in the sequencing reaction of step (b), and (d) carrying out a second sequencing reaction by sequential addition of nucleotides to the second free 3' hydroxyl group to determine the sequence of the second template strand in the second region.

The invention provides a method for sequencing two regions of a polynucleotide template, referred to herein as the first and second regions for sequence determination. The first and second regions for sequence determination may be on the same strand of a single-stranded polynucleotide template, or they may be on complementary strands of a double-stranded or self-complementary polynucleotide template.

If the first and second regions for sequence determination occur on a single polynucleotide strand then they must not be immediately adjacent to each other, meaning that the last nucleotide to be sequenced in the first region is not in phosphodiester linkage with the first nucleotide to be sequenced in the second region. It is an essential feature that the two regions for sequence determination must be separated by at least one nucleotide, and are preferably separated by at least 50, more preferably at least 100 or more preferably at least 500 nucleotides.

If the first and second regions for sequence determination occur on complementary strands of a double-stranded polynucleotide template, or a self-complementary template, then the two regions may or may not be complementary to each other.

A key feature of the method of the invention is that is does not require primer hybridisation to the template to be sequenced in order to provide initiation points for the first and second sequencing reactions. This is a particular advantage when the method is carried out on a solid support, such as a chip-based array, since there is no need to carry out any hybridisation reactions on the solid support.

The starting point for the method of the invention is the provision of a polynucleotide template including a first free 3' hydroxyl group which can serve as an initiation point for a sequencing reaction.

In the context of this invention the term "sequencing reaction" refers to any polynucleotide "sequencing-by-synthesis" reaction which involves sequential addition of nucleotides to a growing polynucleotide chain in the 5' to 3' direction using a polymerase in order to form an extended polynucleotide chain complementary to the template region to be sequenced. The identity of the added nucleotide is preferably determined after each addition step, thus the sequence of the template may be inferred using conventional Watson-Crick base-pairing rules.

The starting polynucleotide template is at least partially double-stranded, or self-complementary. The first free 3' hydroxyl group is provided on one strand that is base-paired to a complementary strand (which can be the same polynucleotide strand if the template is self-complementary), which forms the first strand of the template to be sequenced (first template strand), in the region immediately upstream of the first 3'hydroxyl group. The region of base-pairing between the strand bearing the first hydroxyl group and the first template strand need only be long enough to hold the two strands together under the conditions used for the subsequent sequencing reaction, in order that the hydroxyl group is positioned to initiate the sequencing reaction. Therefore, this region of base-pairing may be as short as from 10 to 13 base-pairs. In embodiments wherein the template is linked to a hairpin linker (see below), the region of base-pairing is provided by the "stem" portion of the hairpin linker.

The first template strand overhangs the first 3' hydroxyl group in order to define a first region of the template to be sequenced. The overhanging portion of the first template strand may be single-stranded. Alternatively, the overhanging region may be annealed to a complementary strand downstream of the free 3' hydroxyl. The latter arrangement may be used if the first sequencing reaction is to be performed using a strand-displacement polymerase. The length of the overhanging strand may be from 100 nucleotides (or base-pairs if double-stranded) up to 1 kb, or even longer. Preferably the overhanging strand will be at least 500 nucleotide (or base-pairs).

The template may be provided as a single polynucleotide molecule which is partially self-complementary. For example, the template polynucleotide molecule may fold back on itself to form a self-complementary hairpin structure at its 3' end.

In one embodiment the starting polynucleotide may be formed by ligating a self-complementary hairpin linker polynucleotide to the desired polynucleotide template to be sequenced, such that the 5' end of the hairpin linker is joined to the 3' end of the first template strand. The first free 3' hydroxyl group is then provided by the 3' end of the hairpin linker. An advantage of this approach is that it may be used for sequencing templates of unknown sequence. Suitable self-complementary hairpin polynucleotide linkers include those described in the applicant's published International application WO 01/57258.

A first sequencing reaction is carried out by sequential addition of nucleotides to the first free 3' hydroxyl group. The nature of the added nucleotide is preferably determined after each nucleotide addition in order to determined the sequence of the first template strand in the first region for sequence determination. This first sequencing reaction can proceed for as long as is technically possible within the limitations of the chosen sequencing methodology, for example until the sequence obtained is no longer accurate or reliable. The first sequencing reaction will preferably involve sequencing of from 10 to 200 or more consecutive bases, preferably from 15 to 35 consecutive bases of the first template strand, preferably from 20 to 30 consecutive bases and more preferably about 25 consecutive bases of the first template strand. The precise number of bases sequenced will be dependent upon the limitations of the chosen sequencing methodology, and more specifically the methodology used to determine the nature of the base added in each nucleotide addition step.

Once the first sequencing reaction is deemed to be complete, sequencing of a second region of the polynucleotide template can be carried out. In order to sequence a second region of the template it is necessary to generate a second free 3' hydroxyl group which serves as an initiation point for a second sequencing reaction. The second free 3' hydroxyl group must be provided on a polynucleotide strand which is base-paired to the second template strand to be sequenced in the region immediately upstream of the second free 3' hydroxyl group. The second template strand overhangs the second free 3' hydroxyl group to define a second region of the template to be sequenced. The first and second template strands may be the same strand of the polynucleotide template if the template is single-stranded, or self-complementary.

It is an essential feature of the invention that the second free 3' hydroxyl group is "spaced apart from" the last nucleotide added in the first sequencing reaction, meaning that the second free 3' hydroxyl group must not be provided by the last nucleotide added in the first sequencing reaction, and that there must be at least one nucleotide separating the last nucleotide added in the first sequencing reaction and the nucleotide which provides the second free 3' hydroxyl group. Preferably the last nucleotide added in the first sequencing reaction and the nucleotide which provides the second free 3' hydroxyl group will be separated by at least 50 nucleotides, more preferably at least 100 nucleotides and more preferably at least 500 nucleotides.

It is also a feature of the invention that the last nucleotide added in the first sequencing reaction and the nucleotide which provides the second free 3' hydroxyl group should be generated in "continuous covalent linkage". This means that the last nucleotide added in the first sequencing reaction and the nucleotide which provides the second free 3' hydroxyl group should form part of a single polynucleotide molecule with continuous backbone phosphodiester linkage, or at least that they should have been so-joined on a single polynucleotide molecule at some stage in the sequencing method. This polynucleotide molecule may be a single strand or it may be a partially self-complementary polynucleotide strand, having a hairpin or stem-loop structure.

The requirement for the last nucleotide added in the first sequencing reaction and the nucleotide which provides the second free 3' hydroxyl group to be in continuous covalent linkage is advantageous for pairwise sequencing of templates of unknown sequence, since it overcomes the problem of designing a primer to initiate sequencing of second region of a template of unknown sequence. Thus, the second free 3' hydroxyl group is NOT provided by hybridisation of a separate primer. This in turn means that when the method of the invention is carried out on an array there is no need to carry out any hybridisation steps after the templates are immobilised on the array.

There are several different ways in which the second free 3' hydroxyl group may be generated, as will be discussed in further detail below.

Non-limiting embodiments of the invention are now described in detail with reference to the accompanying drawings, in which.

Figure 1:
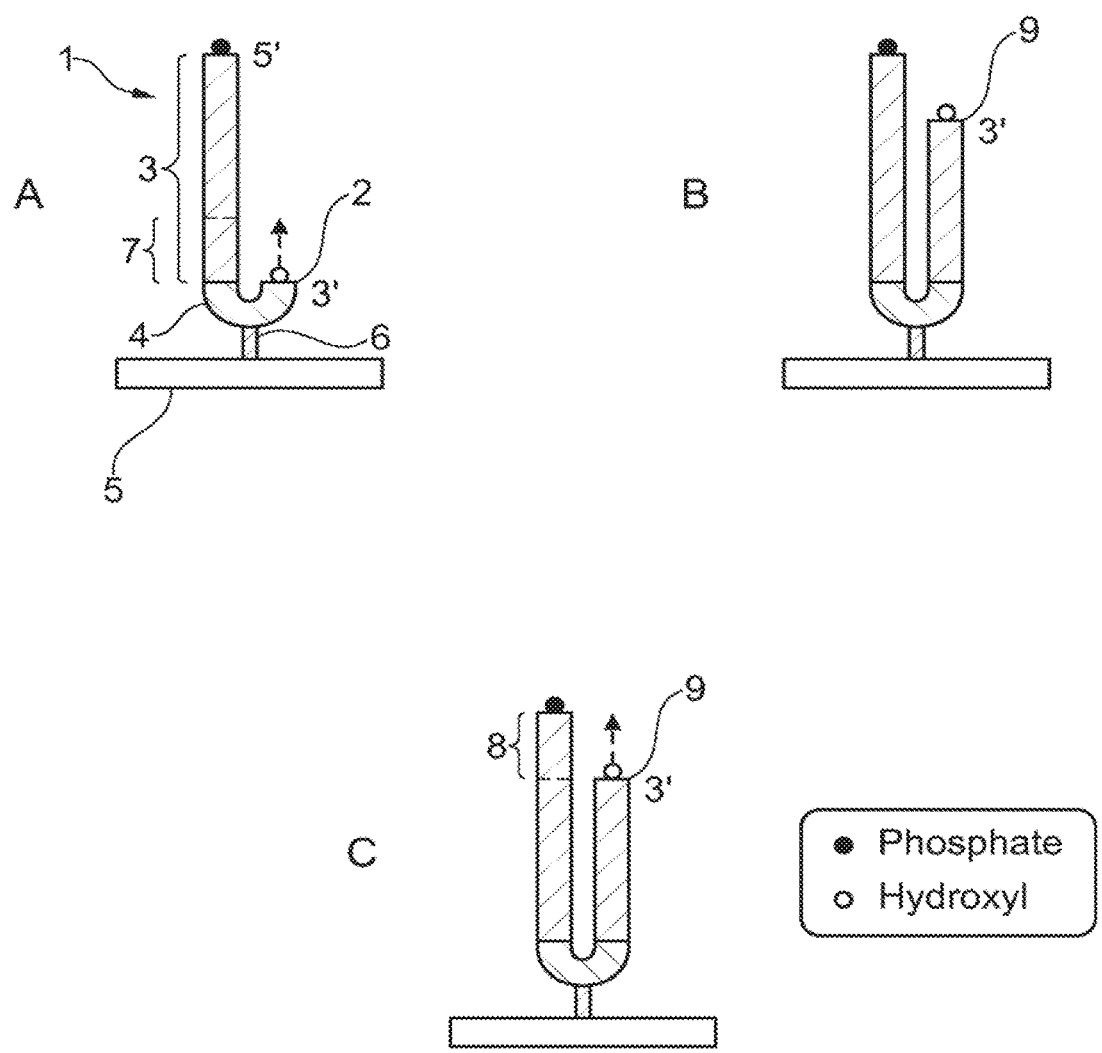
FIGS. 1 and 2 illustrate different embodiments of the sequencing method according to the invention which allow sequencing of first and second regions of a single-stranded polynucleotide template.

Referring to FIG. 1A, a polynucleotide template (1) is provided, having a first free 3' hydroxyl group (2). In this embodiment the template to be sequenced is a single polynucleotide strand (3). In the embodiment shown in FIG. 1A the first free 3' hydroxyl group is provided by the 3' end of a self-complementary hairpin linker (4) which is ligated to the template strand (3) such that the 5' end of the linker (4) is joined to the 3' end of the template strand (3). The linker is also linked to a solid support (5) via any suitable linkage (6). The template strand (3) overhangs the first free 3' hydroxyl group to define a first region of the template to be sequenced (7). Although the specific embodiment shown in FIG. 1A involves use of a hairpin which acts as a primer for sequencing and provides a means for attachment to a solid support the invention is not intended to be limited to the use of hairpins. Any suitable oligonucleotide primer hybridised to the template strand (3) could be used to provide an initiation point for sequencing. Linkage to the solid support could be provided via the primer or via the template strand itself. If linkage to the solid support is provided via the template strand then this may occur at the 5' or the 3' end of the template strand, or even via an internal portion of the template provided that this does not interfere with subsequent sequencing reactions. Template strands generated by solid-phase amplification will generally be linked to a solid support via covalent linkage at their 5' end. Such template strands can be sequenced with the use of "standard" oligonucleotide sequencing primers.

Referring back to the embodiment shown in FIG. 1A, a first sequencing reaction proceeds by sequential addition of nucleotides to the first free 3' hydroxyl group (2). When this sequencing reaction is determined or deemed to be complete, the strand complementary to the template strand (3) is further extended by sequential addition of a known or unknown number of nucleotides to the last nucleotide added in the first sequencing reaction in a nucleotide addition step. This nucleotide addition step occurs without sequencing, i.e. nucleotides are added without any determination of the nature of the nucleotide added in each addition. Thus, the nucleotides added in the addition step need not be modified to permit sequencing and are preferably "unmodified", meaning that they do not contain any labels required for sequencing, e.g. fluorescent labels, or any blocking groups. It is most preferred to use naturally occurring nucleotides in this addition step, although nucleotides bearing "modifications" other than labels or blocking groups could be used as long as the modification does not interfere with incorporation into polynucleotide by the chosen polymerase or addition of subsequent nucleotides (e.g. no chain termination effect) to a material extent.

The free 3' hydroxyl group of the last nucleotide added in the nucleotide addition step forms the second free 3' hydroxyl group (9)—shown in FIG. 1B. The template strand (3) now overhangs the second free 3' hydroxyl group to define a second region of the template to be sequenced (8). Thus, in this embodiment the first and second template strands are provided by a single template strand (3). A second sequencing reaction can then proceed from the second free 3' hydroxyl group.

The addition of further nucleotides following the first sequencing reaction serves to move the sequencing reaction on to a new position on the template. Constraints in the sequencing methodology may limit the number of sequential base additions which can be made with accurate determination of the added nucleotide, meaning that it would not be possible to reach this point in the template in a single continuous sequencing reaction. By switching to addition of further (unmodified) nucleotides without sequencing and then initiating a second sequencing reaction it is possible to sequence a region farther into the template, by carrying out two sequencing reactions separated by a number of "unsequenced" nucleotides.

The number of further nucleotides added between the first and second sequencing reactions is typically at least 50, more preferably at least 100 and more preferably at least 500.

Figure 2:
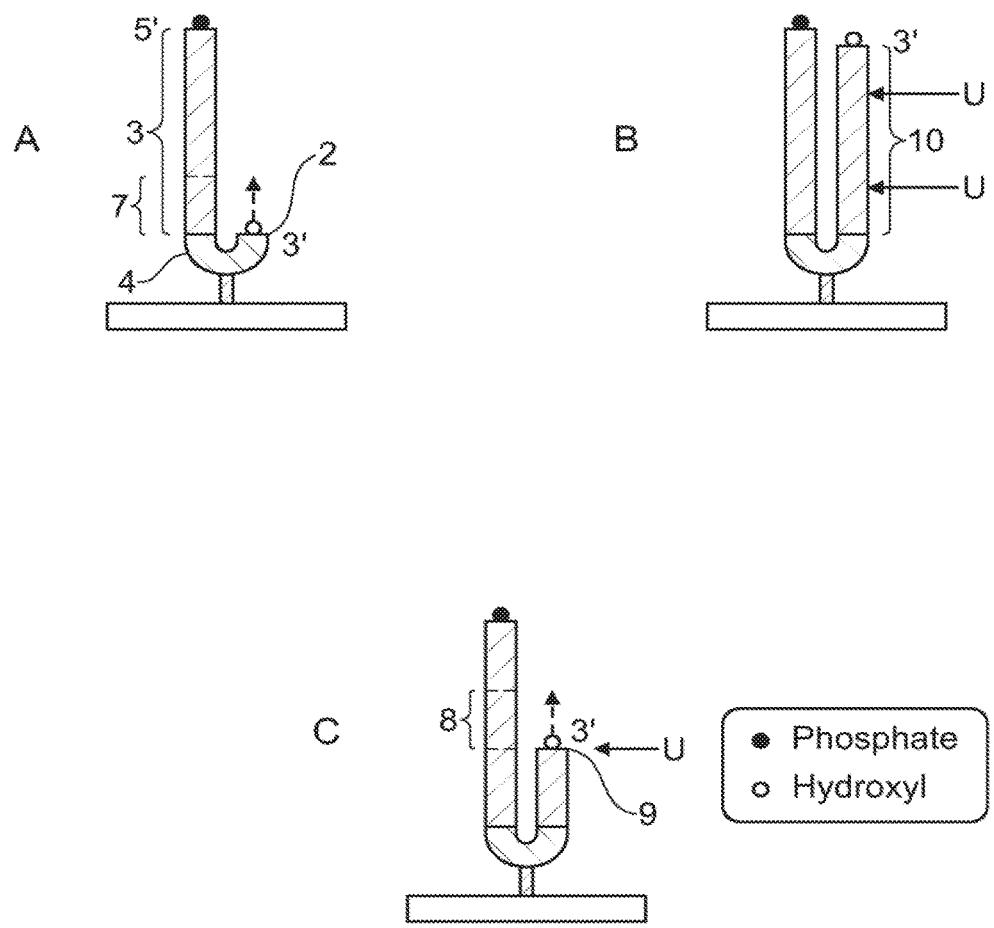

FIG. 2 illustrates a further embodiment of the invention which is substantially similar to the embodiment shown in FIG. 1 and described above, except that the nucleotides added to further extend the complementary strand after completion of the first sequencing reaction comprise a mixture of unmodified deoxynucleotides (dATP, dCTP, dTTP and dGTP) and a small quantity of deoxyuracil, resulting in incorporation of uracil into the complementary strand at some of the positions opposite an A in the template strand. An enzyme which cleaves DNA immediately adjacent to uracil, for example uracil DNA glycosylase, also known as glycosidase or uracil N-glycosylase or uracil DNA N-glycosylase, may then be used to generated a second free 3' hydroxyl group (9) by cleavage of the complementary strand (10).

Figure 3:
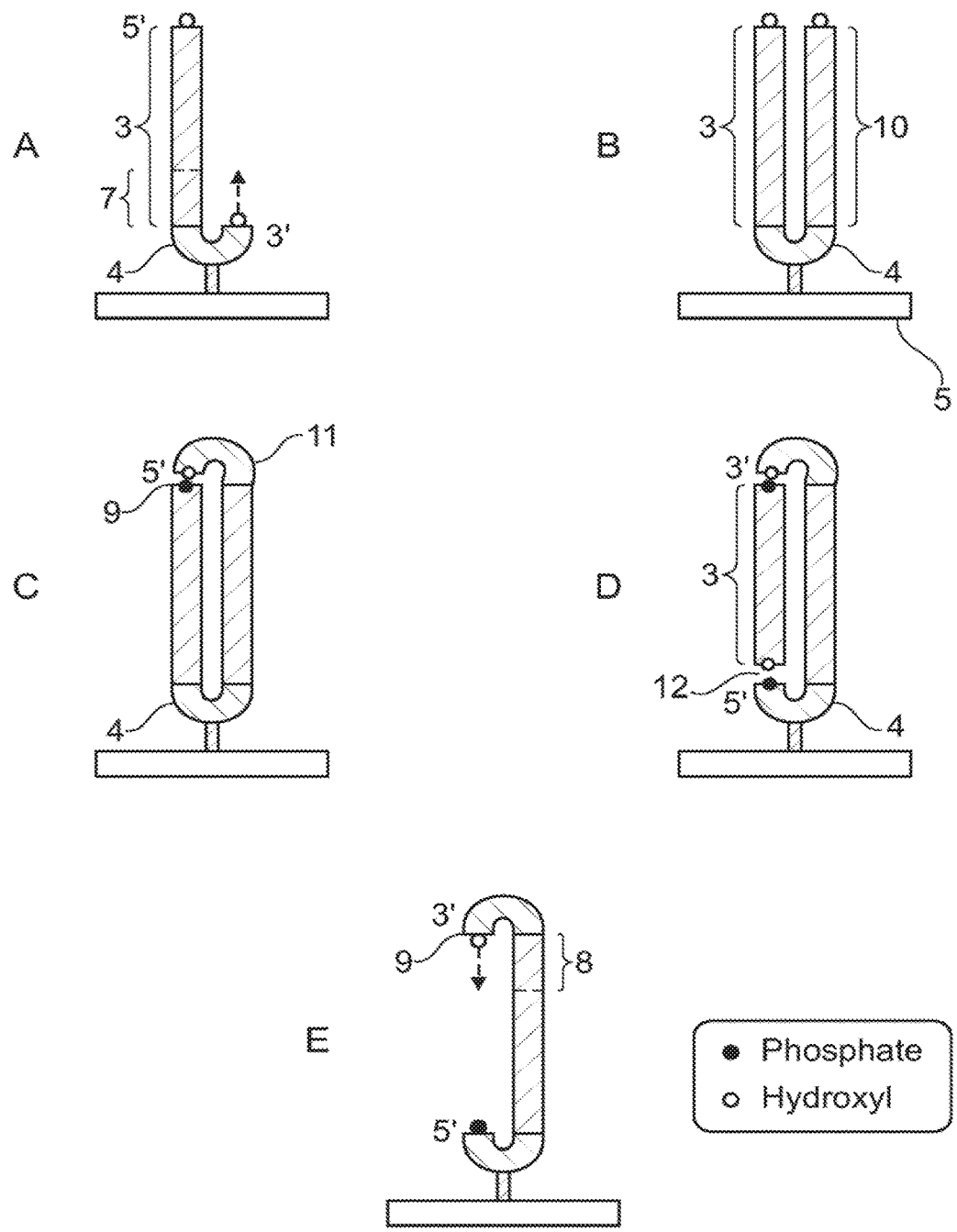
FIGS. 3 to 6 illustrate different embodiments of the sequencing method according to the invention which allow sequencing of first and second regions on complementary strands of a double-stranded polynucleotide template.

FIG. 3 illustrates a still further embodiment of the invention which allows for sequencing of two regions on complementary strands of a double-stranded template. As shown in FIG. 3A, formation of the starting polynucleotide template and sequencing of a first region of the template (7) proceeds as described for the embodiment shown in FIG. 1. After the first sequencing reaction is deemed to be complete further nucleotides are added to the 3' hydroxyl group of the last nucleotide added in the first sequencing reaction in order to fully extend the complementary strand (10) to the full length of the first template strand (3). This extension reaction proceeds without sequencing, i.e. without determination of the nature of the added nucleotides, and results in the production of a blunt-ended fully double-stranded template ligated at one end to a hairpin linker (4), which itself is linked to a solid support (5) (shown FIG. 3B).

The open end of the double-stranded template (distal from the solid support) is then ligated to a second hairpin linker polynucleotide (11) which has a phosphate group at the 5' end and a free hydroxyl group at the 3' end, such that the 5' end of the second hairpin linker is joined to the free 3' end of the extended complementary strand (10). As illustrated in FIG. 3, the 5' end of the first template strand is dephosphorylated (or blocked by some other means) such that it is not capable of forming a phosphodiester linkage with the hydroxyl group at the 3' end of the second hairpin linker. The resulting product has a nicked circular structure (3C). A substantially equivalent structure may also be formed by ligating the second hairpin linker to both the first and second template strands to form a closed circle and then creating a nick in the first template strand (3) or the hairpin linker. The free 3' hydroxyl group (9) of the second hairpin linker provides the second free 3' hydroxyl group for initiation of the second sequencing reaction. The second region of the template to be sequenced (8) is on the complementary strand (10), thus this embodiment allows sequencing of two regions (7, 8) on complementary strands of a double-stranded template. The second free 3' hydroxyl group is formed in continuous covalent linkage with the last nucleotide added in the first sequencing reaction, thus there is no need for hybridisation of a separate sequencing primer in order to initiate sequencing of the second region of the template and no need for any fore-knowledge of the sequence of the template.

The second sequencing reaction can be carried out starting from the nicked circle structure shown in FIG. 3C with the use of a strand displacing polymerase enzyme. In an alternative embodiment, illustrated in FIGS. 3D and 3E, a portion of what was the first template strand (3) may be removed prior to the second sequencing reaction. This may be achieved, for example, by creating a second nick (12) towards the proximal end of the first template strand near the solid support (5). The nick may be created in the first template strand or within the first hairpin linker (4), provided that this does not affect the linkage to the solid support. In a preferred embodiment the nick may be created with the use of an appropriate nicking (single side cutting) restriction enzyme (endonuclease). In order to direct nicking at an appropriate position the first hairpin linker may contain a recognition sequence for a nicking enzyme which directs cleavage of a single strand at a site before, at or beyond the 3' end of the first linker. By including this recognition site in the hairpin linker, generation of the "nick" is independent of the sequence of the template and dependent only on ligation of the linker to the template. This means that the method may be universally applied to templates of unknown, and different, sequence. It will be appreciated that nicking can also be accomplished by blocking one side of a standard restriction enzyme cleavage site (in the hairpin linker sequence or sequences) using methods familiar to those skilled in the art, e.g., by using thiophosphate linkages in one side of the restriction enzyme recognition site, to prevent cutting in that side, but not in the other, or by the use of DNA methylation.

Following the nicking reaction the resulting product may be denatured in order to remove the "free" portion of the first template strand located upstream (5') of the cleavage site, as shown in FIG. 3E.

Figure 4:
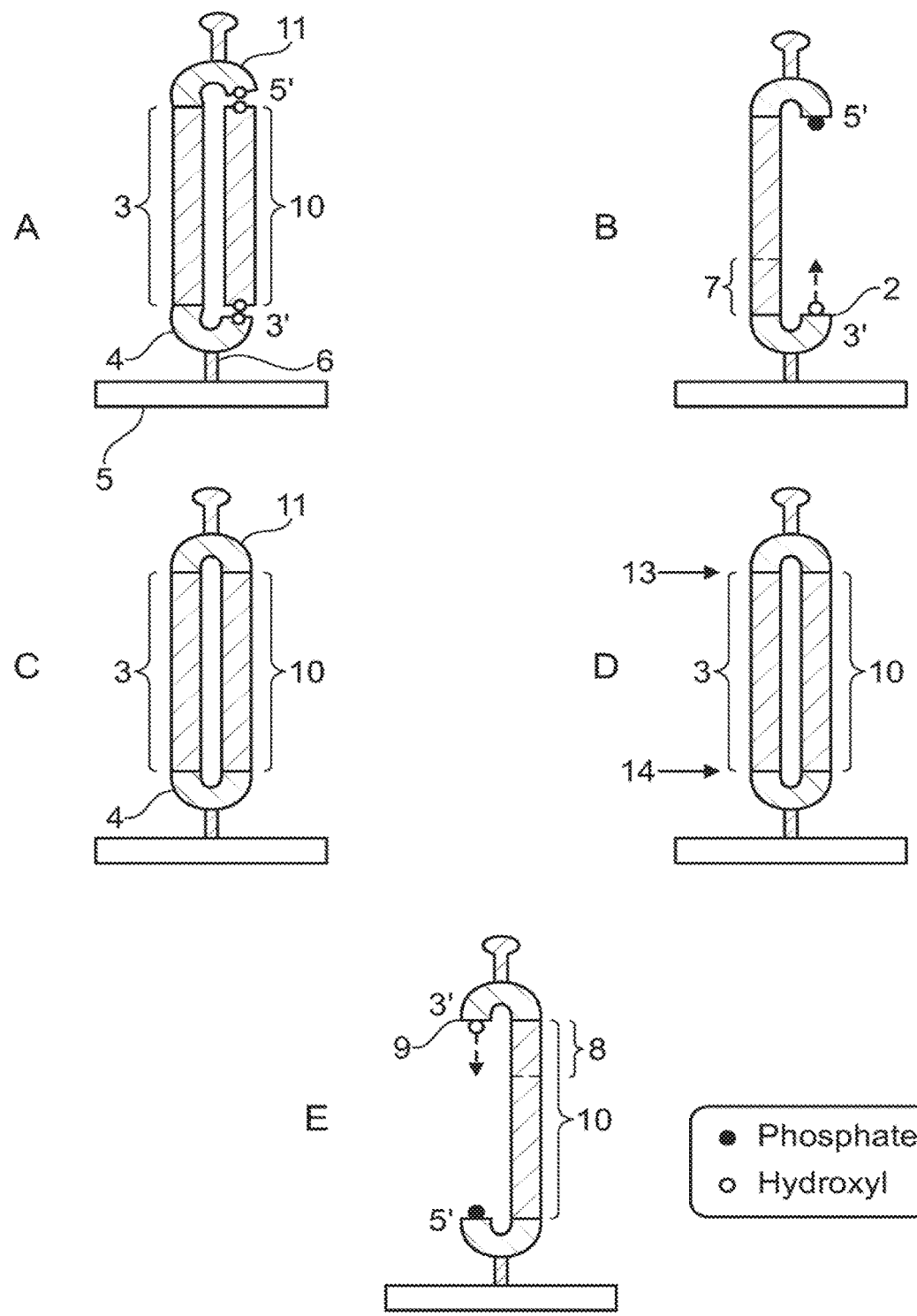

FIG. 4 illustrates a further embodiment of the invention which allows sequencing of two regions on complementary strands of a double-stranded template. This method starts with provision of a fully double-stranded (i.e. blunt ended) polynucleotide template in solution comprising a first template strand (3) annealed to a complementary strand (10). The first template strand has a 5' phosphate group, whereas the complementary strand lacks a 5' phosphate group (or 5' phosphate may be blocked) such that it cannot be joined in phosphodiester linkage to the 3' hydroxyl group of a further nucleotide.

The double-stranded template can be any double-stranded polynucleotide that it is desired to sequence. In a preferred embodiment it will be a fragment of genomic DNA. Double-stranded templates bearing a 5' phosphate on one strand but lacking a 5' phosphate on the complementary strand can be generated in a number of different ways. For example, in one embodiment templates can be generated by limited or controlled digestion of double-stranded DNA fragments bearing 5' phosphates on both strands with a phosphatase enzyme, in order to generate a maximal proportion of strands in which 5' phosphate is removed from one strand only.

In a further embodiment double-stranded DNA fragments may be treated with phosphatase in order to remove 5' phosphate from both strands. The resulting de-phosphorylated product may then be subject to limited or controlled treatment with a kinase in order to restore 5' phosphate, limited treatment ensures that a maximal number of fragments will have 5' phosphate restored on one strand only.

In a still further embodiment an adapter, consisting of paired oligonucleotides having hydroxyl groups at both 3' and 5'ends of both strands may be ligated to one end only of a double-stranded DNA fragment which has 5' phosphate on both strands. A suitable site for attachment of the adapter to one end only may be generated by cutting the template with a suitable restriction enzyme at a site proximal to the chosen end.

In a still further embodiment an adapter oligonucleotide having a 5' phosphate group may be ligated to one end only of a double-stranded DNA template which has been treated with phosphatase to remove all 5' phosphates. Again, suitable site for attachment of the adapter to one end of the template may be generated by cutting the template with a suitable restriction enzyme at a site proximal to the chosen end.

A second hairpin linker polynucleotide (11) is ligated to one end of the double-stranded template. This second linker has hydroxyl groups at both its 3'and 5'ends, thus in the ligation reaction the 3' end of the second linker (OH) is joined to the 5' end of the first template strand (phosphorylated), but the 5' end of the second linker (also OH) remains free. The second hairpin linker may include a marker moiety, for example biotin, which facilitates selection of template molecules that have been successfully ligated to the second linker.

A first hairpin linker (4) is ligated to the second end of the double-stranded template. This first linker has a hydroxyl group at the 3' end and a phosphate group at the 5' end. Thus, in the ligation reaction the 5' end of the first linker (phosphate) is joined to the 3' end of the first template strand (OH) but the 3' end of the first linker (OH) remains free. The first hairpin linker may be attached to a solid support (5) via a suitable linkage (6). Attachment to the solid support is preferably carried out after the first linker (4) has been ligated to the double-stranded template. This provides a means of selection, since only templates that have been correctly ligated to the first linker will be linked to the solid support.

The terms "first" and "second" hairpin linker are used for convenience solely for the purposes of identifying the different structure/function of the two linkers. The designations "first" and "second" do not require the linkers to be joined to the template strands in any particular order. In the embodiment shown in FIG. 4 it may be convenient for the second linker to be ligated to the template before the first linker, since the presence of biotin, or other suitable selectable marker moiety, will enable selection of templates bound to this linker prior to linkage to the solid support.

The product resulting from ligation of the first and second hairpin linkers is a closed circle which is "nicked" in two places, as illustrated in FIG. 4A. The "free" strand between the two nicks (10) may be removed by denaturation to give the structure illustrated in FIG. 4B. Following denaturation the 5' end (17) of the second linker (11) may be treated with a kinase to restore the 5' phosphate group.

The 3' end of the first free linker provides the first free 3' hydroxyl group (2) for initiation of the first sequencing reaction (illustrated FIG. 4B). When the first sequencing reaction is deemed to be complete, further nucleotides are added to the 3' hydroxyl group of the last nucleotide added in the first sequencing reaction in order to fully extend the complementary strand (10) to the full length of the first template strand. This extension reaction proceeds without sequencing, i.e. without determination of the nature of the added nucleotides. The 3'hydroxyl end of this extended strand (which will subsequently form the second template strand) is ligated to the phosphate group newly added to the 5' end of the second hairpin linker (11). Addition of phosphate to the 5' end of second linker could be carried out after extension of the complementary strand, immediately prior to the ligation reaction, if convenient. The product of this ligation is a fully closed circle structure, as illustrated in FIG. 4C.

In order to generate a second free 3' hydroxyl group for initiation of the second sequencing reaction the closed circle structure shown in FIG. 4C may be nicked at a suitable position in the first template strand (3). The position of this first "nick" (13) will determine the position of the second region to be sequenced on the complementary strand (10, now referred to as the second template strand). Again, the nick may be generated with the use of a suitable nicking or side-cutter enzyme. The second hairpin linker (11) may include a recognition site for a nicking enzyme which directs nicking/cleavage at a site before, at or beyond the 3' end of the second linker. Thus, generation of the nick (13) is dependent only on the presence of the hairpin linker and is independent of the sequence of the template.

Following generation of a first nick (13), the second sequencing reaction can proceed from the second free 3' hydroxyl group generated as a result of the nicking reaction with the use of a strand displacing polymerase enzyme. Alternatively, a portion of the first template strand downstream from (3' of) this first nick can be removed altogether prior to the second sequencing reaction. This can be achieved by generating a second nick (14) spaced apart from (downstream of) the first nick (13). Again a suitable nicking enzyme can be used for this purpose. In order to form the second nick the first hairpin linker (4) may include a recognition site for a nicking enzyme which directs cleavage at a site before, at or beyond the 5' end of the first hairpin linker. Following generation of the second nick, the portion of the first template strand located between the two nicks may be removed by denaturation, leaving the structure illustrated in FIG. 4E. The second sequencing reaction may then proceed from the second free 3' hydroxyl group (9).

Figure 5:
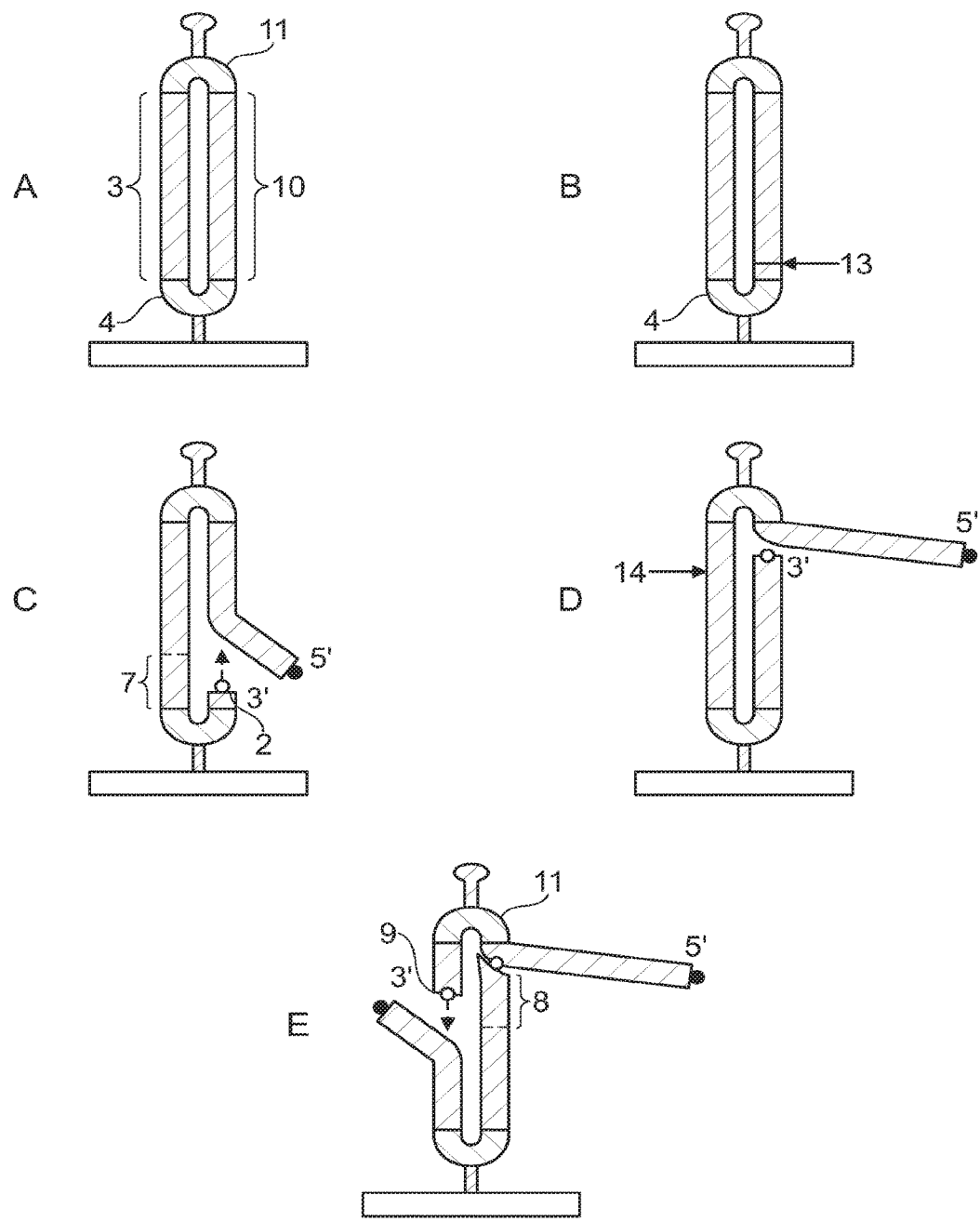

FIG. 5 illustrates a further embodiment of the invention which allows sequencing of two regions on complementary strands of a double-stranded template. The starting template for this method is a partially self-complementary covalently closed circle structure as illustrated in FIG. 5A. This structure can easily be formed by ligation of first (4) and second (11) hairpin linkers to the ends of a fully double-stranded, blunt ended template comprising first (3) and second (10) template strands.

A first free 3' hydroxyl group is generated by cleavage of one template strand (10) of the covalently closed circle to generate a first "nick" (13) with the use of an appropriate nicking or side-cutter enzyme. Formation of this nick can be directed by including a suitable recognition site in the first hairpin linker (4) which directs cleavage (nicking) at a site before, at or beyond the 3' end of the linker. This first "nick" generates the first free 3' hydroxyl group (2) for initiation of the first sequencing reaction. Sequencing may then proceed from this initiation point using a strand displacement polymerase enzyme.

Once this first sequencing reaction is deemed to be complete a second nick (14) may be generated within the opposite (complementary) template strand (3). Formation of this nick can be achieved by the inclusion of a suitable recognition site in the second hairpin linker (11) which directs cleavage (nicking) at a site before, at or beyond the 3' end of this linker. This second nick generates the second free 3' hydroxyl group (9) for initiation of the second sequencing reaction. Sequencing may then proceed from this initiation point using a strand displacement polymerase enzyme. Thus, this method allows sequencing of two target regions (7,8) on opposite strands of a double-stranded template.

In this method the nucleotides which will ultimately provide the first and second free 3' hydroxyl groups are in continuous covalent linkage before initiation of the first sequencing reaction through the formation of the closed circle structure illustrated in FIG. 5A. Thus, this embodiment provides the same technical advantages as the other embodiments of the invention, since it permits sequencing of two distinct regions of a template of unknown sequence, without the need for hybridisation of two (or more) separate sequencing primers to provide initiation points for sequencing.

Figure 6:
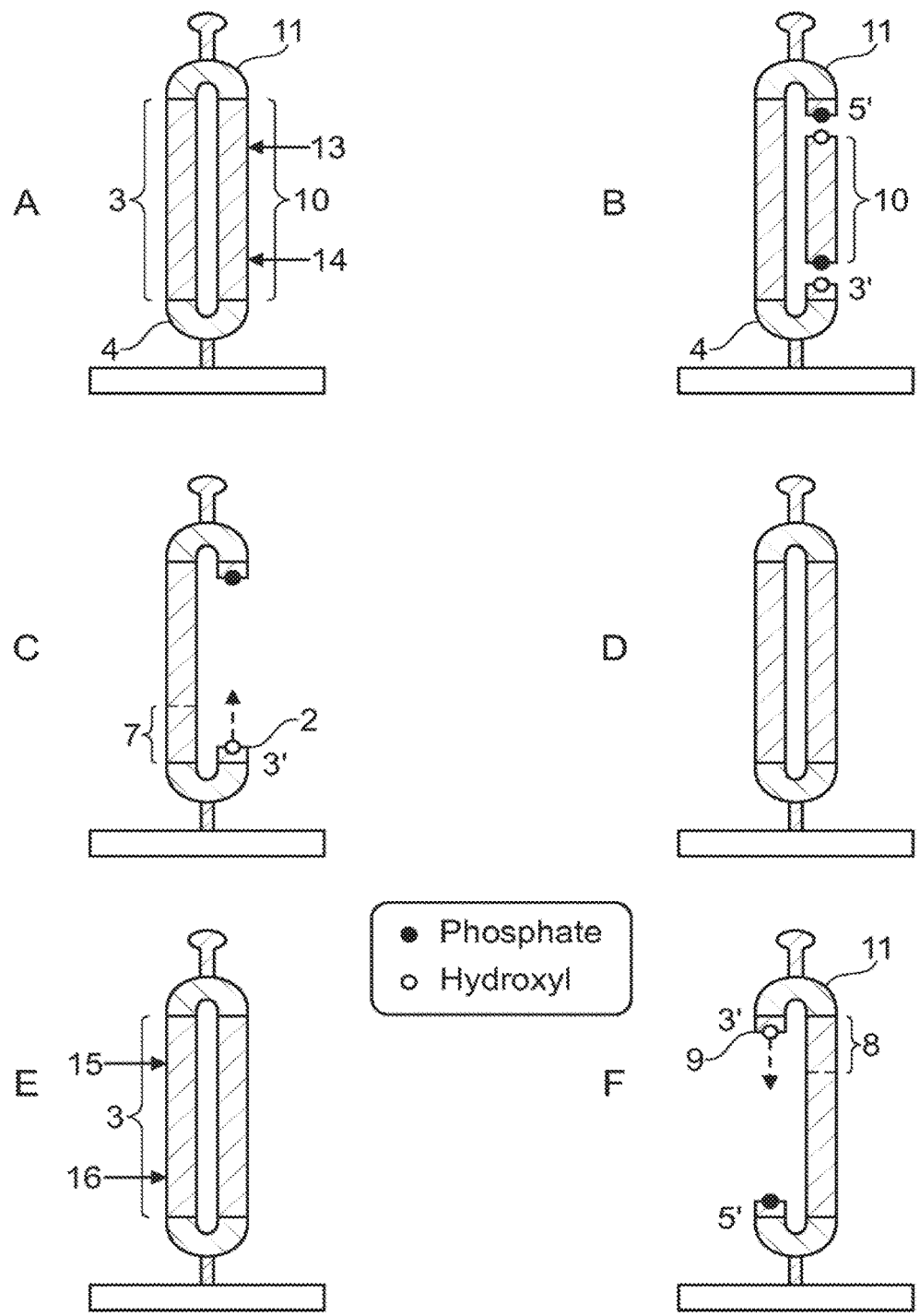

FIG. 6 illustrates a further embodiment of the invention which allows sequencing of two regions on complementary strands of a double-stranded template. The starting template for this method is a partially self-complementary covalently closed circle structure (6A) identical to that illustrated in FIG. 5A. The covalently closed circle may be formed by ligating first (4) and second (11) hairpin linkers to a double-stranded polynucleotide comprising first (3) and second (10) template strands.

The second template strand (10) is then "nicked" at two sites (13,14) spaced apart from each other. These nicks can be formed by the inclusion of suitable recognition sequences in the first (4) and second (11) hairpin linkers. The portion of the template strand (10) located between the two nicks is then removed by denaturation to generate the structure shown in FIG. 6C. A first sequencing reaction may then proceed from the first free 3' hydroxyl group (2).

When the first sequencing reaction is complete, the method continues substantially as described above with reference to FIG. 4, from completion of the first sequencing reaction. In brief summary, the covalently closed structure is re-generated by extending the strand formed in the first sequencing reaction to produce a fully double-stranded template and then ligating the 3' end of this extended strand to the free 5' end of the second linker (11). A further nick may then be formed in the first template strand (3) at a third nicking site (15). Again formation of this nick can be directed by including a suitable recognition sequence in the second linker (11) which directs cleavage before, at or beyond its 3' end. The free 3' hydroxyl group generated as a result of this nicking then provides the second free 3' hydroxyl group (9) for initiation of the second sequencing reaction.

The second sequencing reaction may be carried out with the use of a strand displacement polymerase. Alternatively, a portion of the strand downstream of the third nicking site (15) may be removed by nicking this strand at a still further (fourth) nicking site (16). Again formation of this nick can be directed by including a suitable recognition sequence in the first hairpin linker (4) which directs cleavage before, at or beyond its 5' end. The "free" portion of the template strand (3) located between the two nicking sites (15,16) may then be removed by denaturation and sequencing can proceed from the second free 3' hydroxyl group (9). Thus, this embodiment results in sequencing of two regions (7,8) located on opposite strands of a double-stranded template.

The following preferred features apply mutatis mutandis to all embodiments of the invention:

The polynucleotide template to be sequenced using the method of the invention may be any polynucleotide that it is desired to sequence. A key advantage of the invention is that the template may be of unknown sequence. However, the method may also be used to sequence templates of known or partially known sequence, for example in re-sequencing applications. With the use of arrays it is possible to sequence multiple templates of the same or different sequence in parallel. A particularly preferred application of the method is in the sequencing of fragments of genomic DNA.

Certain embodiments of the method of the invention make use of hairpin linker polynucleotides, as described above. Self-complementary hairpin polynucleotide linkers generally have a "stem-loop" structure, formed by base-pairing of complementary polynucleotides that are covalently linked at one end. The covalent linkage may be provided by a short single-stranded polynucleotide loop, or may be a non-polynucleotide chemical linkage. Preferred chemical linkages include an arrangement of two hexaethylene glycol (heg) spacers separated by an amino deoxy-thymidine nucleotide. Preferred hairpin linker polynucleotides are those described in the applicant's published International application WO 01/57258. The hairpin linker is effectively "self-priming", including a free 3' hydroxyl group to which further nucleotides may be added. This 3' hydroxyl group provides an initiation point for sequencing of any polynucleotide template strand ligated to the 5' end of the hairpin, independent of the sequence of the template strand. The precise nucleotide sequence of the hairpin linker is not material to the invention.

Hairpin linkers can also provide a means of linking the template strands to be sequenced to a solid support, for example to form an array. For example, hairpins including the above-described linkage consisting of two hexaethylene glycol (heg) spacers separated by an amino deoxy-thymidine nucleotide can be linked to epoxide-modified surfaces (e.g.

as described in WO 01/57248). The solid support can be of any suitable material, for example glass, ceramic, silicon, plastics or other polymeric material. Suitable support materials are also described in the applicant's published International applications WO 00/06770. The support may take any convenient form. For example it may be substantially planar, such as a slide or "DNA chip", or may be a three dimensional support, or a support formed from multiple discrete units, for example beads of glass, plastics, magnetic material etc.

Templates may be attached to a solid support via any suitable linkage method known in the art. Preferably linkage will be via covalent attachment. The templates may be attached to the support directly or via a hairpin linker. If hairpin linkers are used then they may be attached to the solid support before they are linked to template(s) to be sequenced. For example, hairpin linkers may be attached to the solid support to form an array prior to attachment of the template(s). Techniques for forming arrays of hairpin linkers are described in WO 01/57248. The templates/linkers are preferably attached to the solid support via a covalent linkage. Linkage may be made via any part of the template or hairpin, provided that this does not interfere with the ability of the template/linker to participate in a sequencing reaction. If hairpins are used, the linkage may advantageously be made via an internal portion of the hairpin, leaving the 3' end free to initiate a sequencing reaction and the 5' end free for attachment to the template. In the case of template strands generated by solid-phase amplification attachment to the solid support will usually be via covalent linkage with the 5' end of the template.

If the templates are "arrayed" on a solid support then the array may take any convenient form. An advantage of the method of the invention is that large numbers of templates of different sequence can be processed in parallel, since the method is independent of the sequence of the template and does not require any sequence-specific hybridisation steps to take place on the array. Thus, the method is applicable to all types of "high density" arrays, including single-molecule arrays and clustered arrays.

Single molecule arrays are formed by immobilisation of a single polynucleotide molecule at each discrete site that is detectable on the array. Single-molecule arrays comprised of nucleic acid molecules that are individually resolvable by optical means and the use of such arrays in sequencing are described, for example, in WO 00/06770. Single molecule arrays comprised of individually resolvable nucleic acid molecules including a hairpin loop structure are described in WO 01/57248. The method of the invention is suitable for sequencing template molecules on single molecule arrays prepared according to the disclosures of WO 00/06770 of WO 01/57248.

However, it is to be understood that the scope of the invention is not intended to be limited to the use of the method in connection with single molecule arrays. The method may be used for sequencing on essentially any type of array formed by immobilisation of nucleic acid molecules on a solid support, and more particularly any type of high-density array. In addition to single molecule arrays suitable arrays may include, for example, multi-polynucleotide or clustered arrays in which distinct regions on the array comprise multiple copies of one individual polynucleotide molecule or even multiple copies of a small number of different polynucleotide molecules (e.g. multiple copies of two complementary nucleic acid strands).

In particular, the method of the invention may be utilised for sequencing on multi polynucleotide or "clustered" arrays. Multi-polynucleotide or clustered arrays of nucleic acid molecules may be produced using techniques generally known in the art. By way of example, WO 98/44151 and WO 00/18957 both describe methods of nucleic acid amplification which allow amplification products to be immobilised on a solid support in order to form arrays comprised of clusters or "colonies" of immobilised nucleic acid molecules. The nucleic acid molecules present on the clustered arrays prepared according to these methods may be suitable templates for sequencing using the method of the invention. However, the invention is not intended to be limited to use of the method in sequencing reactions carried out on clustered arrays prepared according to these specific methods.

When using arrays formed from nucleic acid "colonies", such as arrays prepared according to the teaching in WO 98/44151 and WO 00/18957, it is not necessary to use a hairpin linker polynucleotide to link the template molecule to the array and provide the first free 3' hydroxyl group for sequencing. The arrays of WO 98/44151 and WO 00/18957 are formed by "on-chip" amplification using primers and templates immobilised on a solid support. Once amplification is complete, the colonies may comprise pluralities of double-stranded nucleic acid molecules. These double-stranded molecules may be processed to form templates suitable for use in the methods of the invention, either by forming a "nick" in one strand only of the double-stranded molecules or by removing a portion of one strand altogether. Either way, a free 3' hydroxyl group will be formed on one strand which serves as an initiation point for the first sequencing reaction. After the first sequencing reaction is complete, formation of the second free 3' hydroxyl group can proceed using some of the alternatives described above, with appropriate modification.

As outlined above, sequencing can be carried out using any suitable "sequencing-by-synthesis" technique, wherein nucleotides are added successively to a free 3' hydroxyl group, resulting in synthesis of a polynucleotide chain in the 5' to 3' direction and the nature of the nucleotide added is preferably determined after each addition.

One preferred sequencing method which can be used in the methods of the invention relies on the use of modified nucleotides that can act as chain terminators. Once the modified nucleotide has been incorporated into the growing polynucleotide chain complementary to the region of the template being sequenced there is no free 3'-OH group available to direct further sequence extension and therefore the polymerase can not add further nucleotides. Once the nature of the base incorporated into the growing chain has been determined, the 3' block may be removed to allow addition of the next successive nucleotide. By ordering the products derived using these modified nucleotides it is possible to deduce the DNA sequence of the DNA template. Such reactions can be done in a single experiment if each of the modified nucleotides has attached a different label, known to correspond to the particular base, to facilitate discrimination between the bases added at each incorporation step. Alternatively, a separate reaction may be carried out containing each of the modified nucleotides separately.

The modified nucleotides carry a label to facilitate their detection. Preferably this is a fluorescent label. Each nucleotide type may carry a different fluorescent label. However the detectable label need not be a fluorescent label. Any label can be used which allows the detection of the incorporation of the nucleotide into the DNA sequence.

One method for detecting the fluorescently labelled nucleotides comprises using laser light of a wavelength specific for the labelled nucleotides, or the use of other suitable sources of illumination. The fluorescence from the label on the nucleotide may be detected by a CCD camera or other suitable detection means.

The methods of the invention are not limited to use of the sequencing method outlined above, but can be used in conjunction with essentially any sequencing methodology which relies on successive incorporation of nucleotides into a polynucleotide chain. Suitable techniques include, for example, Pyrosequencingm, FISSEQ (fluorescent in situ sequencing), MPSS (massively parallel signature sequencing) and sequencing by ligation-based methods.

The invention will be further understood with reference to the following non-limiting experimental example:

EXAMPLE

Methods and Materials
(1) Extension of Polynucleotide Strands with Polymerase and All Four Nucleotides-without Sequencing.

A polymerase (e.g., Taq DNA polymerase, Pfu plymerase, Klenow fragment of *E.coli* Pol I, etc.) is added at a suitable concentration in a buffer designed to be used with that enzyme. All four deoxynucleotide triphosphates are added at a concentration in the 1-11 micromolar range. Extension is for a time (10 sec to a few minutes) that will allow approximately 500 base pairs to be incorporated.
(2) Extension of Polynucleotide Strands with Polymerase, Deoxyuracil and All Four Nucleotides.

As in previous description (3), but with a small amount (1 part in 100, e.g. compared with standard deoxythymidine triphosphate) of deoxyuracil triphosphate mixed in. The amount of U nucleotide is adjusted to provide incorporation of U at a rate of the order of 1 U every 500 nucleotides added.
(3) Cleavage of U-ontaining DNA with Uracil DNA Glycosylase (UDG).

After an appropriate wash, chips containing DNA can be incubated in 14 parts UDG Buffer (70 mM Hepes-KOH pH 8.0, 1 mM dithiothreitol, 1 mM EDTA), 1 part uracil DNA glycosylase (BRL). After e.g. two hours of incubation at 37° C. the chips are optionally washed with a high pH wash solution and heated to 94° C. for up to 10 min to kill the enzyme. This step may not be necessary for a chip. They are then subjected to appropriate washes in an appropriate buffer and made ready for the next step.
(4) On-chip Ligation.

Hairpin DNA on the surface at a density to allow appropriate single molecule array analysis ($10^7$-$10^9$ molecules per square cm) and double-stranded genomic DNA are mixed together. The molecules to be ligated must contain the appropriate phosphate or hydroxyl termini as described above. The DNA molecules are incubated in the presence of a 1:2 dilution of "2× Quick Ligation Reaction Buffer" (NEB=New England Biolabs, Beverly, Mass.) and a 1:20 dilution of NEB "Quick T4 DNA Ligase", both components of the NEB kit called "Quick Ligation Kit", at room temperature for approximately 1 h. Subsequently, washing is performed in a suitable wash reagent(s) or buffer(s), using suitable times and temperatures.
(5) Nicking Reaction.

Nicking of DNA on a surface via specific recognition sequences in the known part of the DNA is described here. The surface equivalent of roughly a solution amount of 1.25 pmoles of DNA is digested at 55° C. for 30 minutes with N.BstNBI (50 Units/mL final concentration) in its supplied buffer (NEBuffer N.BstNBI at "1×" final concentration) from the manufacturer (NEB). This experiment can also be performed with little modification in a flow-cell where the substrate comprises DNA ligated to DNA hairpins that are covalently attached to the glass surface of the flow-cell. In this case, the attachment of the DNA to a solid support, the glass, obviates the need to employ a DNA purification step between enzyme steps; instead, products can be removed and new reagents added by flowing solutions through the cell. Suitable wash buffers as known in the art can be employed.

It will be appreciated that nicking can also be accomplished by blocking one side of a standard restriction enzyme cleavage site (in the hairpin oligonucleotide sequence or sequences) using methods familiar to those skilled in the art, e.g., by using thiophosphate linkages in one side of the restriction enzyme's recognition site, to prevent cutting in that side, but not in the other.
(6) Strand-displacement Polymerisation.

Strand-displacement polymerisation is carried out using a suitable strand-displacement polymerase (e.g., BST Polymerase). The reaction conditions are, e.g., "1× Thermopol buffer" (final concentrations: 20 mM Tris-HCl pH 8.8 measured @ 25° C., 10 mM KCl, 10 mM $(NH_4)_2SO_4$, 2 mM $MgSO_4$, 0.1% Triton X-100), all four dNTPs at a concentration of between 1 and 200 micromolar, 160 Units/mL (final concentration) of BST large fragment polymerase (NEB). Reactions are performed, for 2 hrs. at 60° C., for example, followed by washing in a suitable wash buffer, using suitable times and temperatures.
(7) Denaturation.

Denaturation may be performed by any of the methods known to those skilled in the art. Typically there are three preferred methods:

Chips are washed in very low ionic strength or distilled water.

Chips are incubated at high temperature (80-90° C., typically) for a few minutes in an appropriate buffer or at 40-70° C. in 50% deionized formamide dissolved in water.

Chips are incubated at high pH briefly, i.e. pH greater than 10. This latter method is least preferred as it may be damaging to the surface chemistry of the chip.
(8) Phosphatasing and Kinasing.

See e.g., Maniatis, T., E. F. Fritsch and J. Sambrook. 1982. Molecular Cloning: A Laboratory Manual. Cold Spring Harbor Laboratory, Cold Spring Harbor, N.Y.

The invention claimed is:

1. A method for pairwise sequencing of a polynucleotide template, the method comprising:
   (a) providing a polynucleotide template immobilized on a surface, said polynucleotide template comprising
   a first template strand having a first region, wherein the first template strand lacks a 5' phosphate group or comprises a blocked 5' phosphate group such that the first template strand is not capable of being ligated to a free 3' hydroxyl group, and
   a first self-complementary hairpin polynucleotide linker comprising a loop region and a stem region, wherein the 5' end of one strand of the stem region is linked to the 3' end of said first template strand and the 3' end of the other strand of the stem region comprises a first free 3' hydroxyl group used for initiating sequencing of the first region of the first template strand,
   (b) performing a first sequencing-by-synthesis reaction comprising sequential incorporation of different complementary reversibly-terminated nucleotides into the 3' end of said first self-complementary hairpin polynucleotide linker, thereby determining the sequence of the first region of the first template strand, wherein each of said nucleotides comprises a fluorescent label and a 3' blocking group, the blocking group prevents any further nucleotide incorporation into the 3' end of the polynucleotide template, and wherein said sequential incorporation comprise (i) incorporating one of said nucleotides into the first free 3' hydroxyl group and detecting a fluorescent signal generated from the fluorescent label using a CCD camera or other fluorescence detection means, and (ii) cleaving the fluorescent label and the 3' blocking group from said one of said nucleotides in the 3' end of said polynucleotide template, thereby yielding a free 3' hydroxyl group before another of said nucleotides is incorporated into the 3' end of said polynucleotide template, (c) adding an unlabeled nucleotide to the free 3' hydroxyl group in the last nucleotide added in step (b) and performing an extension reaction in the presence of different unlabeled nucleotides, thereby generating a second template strand having a free 3' hydroxyl group, wherein the second template strand is complementary to the full length of said first template strand and comprises a second region, (d) forming a ligation product by ligating a second self-complementary hairpin polynucleotide linker having a free 3' hydroxyl group to the free 3' hydroxyl group of the second template strand, whereby the free 3' hydroxyl group of the second self-complementary hairpin polynucleotide linker provides a second free 3' hydroxyl group used for initiating sequencing of the second region of the second template strand, and (e) performing a second sequencing-by-synthesis reaction comprising sequential incorporation of different complementary reversibly-terminated nucleotides into the 3' end of the second self-complementary hairpin polynucleotide linker of said ligation product using a strand-displacing polymerase, thereby generating an extended complementary strand and determining the sequence of the second region of the second template strand, wherein each of said nucleotides comprises a fluorescent label and a 3' blocking group, the blocking group prevents any further nucleotide incorporation into the 3' end of said ligation product the extended complementary strand, and wherein said sequential incorporation after step (d) comprises (i) incorporating one of said nucleotides into the second free 3' hydroxyl group and detecting a fluorescent signal generated from the fluorescent label using a CCD camera or other fluorescence detection means, and (ii) cleaving the fluorescent label and the 3' blocking group from said one of said nucleotides in the 3' end of said ligation product, thereby yielding a free 3' hydroxyl group before another of said nucleotides is incorporated into the 3' end of said ligation product;

wherein the first template strand ranges in length from 100 nucleotides to 1 kb.

2. The method of claim 1, wherein the polynucleotide template forms part of an array.

3. The method of claim 1, wherein the first sequencing-by-synthesis reaction of step (b) comprises incorporation of 10 to 200 consecutive nucleotides.

4. The method of claim 1, wherein the second sequencing-by-synthesis reaction of step (e) comprises incorporation of 10 to 200 consecutive nucleotides.

5. The method of claim 1, wherein the extension reaction of step (c) comprises incorporation of at least 100 consecutive nucleotides.

6. The method of claim 1, wherein the extension reaction of step (c) comprises incorporation of at least 200 consecutive nucleotides.

7. The method of claim 1, wherein the polynucleotide template is directly linked to the surface of a solid support.

8. The method of claim 1, wherein the extension reaction of step (c) is performed without determining the identities of the unlabeled nucleotides added in step (c).

9. A method for pairwise sequencing of a polynucleotide template, the method comprising:

(a) providing a polynucleotide template immobilized on a surface, said polynucleotide template comprising a first template strand having a first region, and a first self-complementary hairpin polynucleotide linker comprising a loop region and a stem region, wherein the 5' end of one strand of the stem region is linked to the 3' end of said first template strand and the 3' end of the other strand of the stem region comprises a first free 3' hydroxyl group used for initiating sequencing of the first region of the first template strand, (b) performing a first sequencing-by-synthesis reaction comprising sequential incorporation of different complementary reversibly-terminated nucleotides into the 3' end of said first self-complementary hairpin polynucleotide linker, thereby determining the sequence of the first region of the first template strand, wherein each of said nucleotides comprises a fluorescent label and a 3' blocking group, the blocking group prevents any further nucleotide incorporation into the 3' end of the polynucleotide template, and wherein said sequential incorporation comprise (i) incorporating one of said nucleotides into the first free 3' hydroxyl group and detecting a fluorescent signal generated from the fluorescent label using a CCD camera or other fluorescence detection means, and (ii) cleaving the fluorescent label and the 3' blocking group from said one of said n nucleotides in the 3' end of said polynucleotide template, thereby yielding a free 3' hydroxyl group before another of said nucleotides is incorporated into the 3' end of said polynucleotide template, (c) adding an unlabeled nucleotide to the free 3' hydroxyl group in the last nucleotide added in step (b) and performing an extension reaction in the presence of different unlabeled nucleotides, thereby generating a second template strand having a free 3' hydroxyl group, wherein the second template strand is complementary to the full length of said first template strand and comprises a second region, (d) forming a ligation product by ligating a second self-complementary hairpin polynucleotide linker having a free 3' hydroxyl group to the free 3' hydroxyl group of the second template strand, whereby the free 3' hydroxyl group of the second self-complementary hairpin polynucleotide linker provides a second free 3' hydroxyl group used for initiating sequencing of the second region of the second template strand, (e) producing a truncated ligation product by removing a portion of the first template strand from said ligation product, and (f) performing a second sequencing-by-synthesis reaction comprising sequential incorporation of different complementary reversibly-terminated nucleotides into the 3' end of the second self-complementary hairpin polynucleotide linker of said truncated ligation product, thereby generating an extended complementary strand and determining the sequence of the second region of the second template strand, wherein each of said nucleotides comprises a fluorescent label and a 3' blocking group, the blocking group prevents any further nucleotide incorporation into the 3' end of said truncated ligation product, and wherein said sequential incorporation after step (d) comprises (i) incorporating one of said nucleotides into the second free 3' hydroxyl group and detecting a fluorescent signal generated from the fluorescent label using a CCD camera or other fluorescence detection means, and (ii) cleaving the fluorescent label and the 3' blocking group from said one of said nucleotides in the 3' end of said truncated ligation product, thereby yielding a free 3' hydroxyl group before another of said nucleotides is incorporated into the 3' end of said truncated ligation product;

wherein the first template strand ranges in length from 100 nucleotides to 1 kb.

10. The method of claim 9, wherein the portion of the first template strand is removed by cleavage of the polynucleotide template of said ligation product with a nicking endonuclease followed by denaturation of said truncated ligation product and the portion of the first template strand is located upstream of the cleavage site of said nicking endonuclease.

11. The method of claim 9, wherein the first self-complementary hairpin polynucleotide linker comprises a recognition site for a nicking endonuclease which directs a cleavage by the nicking endonuclease at a site before, at or beyond the 5' end of the first self-complementary hairpin polynucleotide linker.

12. The method of claim 9, wherein the polynucleotide template forms part of an array.

13. The method of claim 9, wherein the first sequencing-by-synthesis reaction of step (b) comprises incorporation of 10 to 200 consecutive nucleotides.

14. The method of claim 9, wherein the second sequencing-by-synthesis reaction of step (e) comprises incorporation of 10 to 200 consecutive nucleotides.

15. The method of claim 9, wherein the extension reaction of step (c) comprises incorporation of at least 100 consecutive nucleotides.

16. The method of claim 9, wherein the extension reaction of step (c) comprises incorporation of at least 200 consecutive nucleotides.

17. The method of claim 9, wherein the polynucleotide template is directly linked to the surface of a solid support.

18. The method of claim 9, wherein the extension reaction of step (c) is performed without determining the identities of the unlabeled nucleotides added in step (c).

\* \* \* \* \*

UNITED STATES PATENT AND TRADEMARK OFFICE
CERTIFICATE OF CORRECTION

PATENT NO. : 10,793,904 B2
APPLICATION NO. : 15/677788
DATED : October 6, 2020
INVENTOR(S) : Harold Philip Swerdlow Page 1 of 1

It is certified that error appears in the above-identified patent and that said Letters Patent is hereby corrected as shown below:

In the Claims

In Column 17, Lines 44-45:
Delete "product the extended complementary strand," and insert -- product, --, therefor.

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*